United States Patent [19]

Garcia et al.

[11] Patent Number: 5,116,987

[45] Date of Patent: May 26, 1992

[54] METHOD OF PREPARING CHROMAN DERIVATIVES, AND SYNTHESIS INTERMEDIATES

[75] Inventors: Georges Garcia, Saint-Gely-Du-Fesc; Daniel Mettefeu, Montpellier; Richard Roux, Vailhauques, all of France

[73] Assignee: Sanofi, Paris, France

[21] Appl. No.: 763,202

[22] Filed: Sep. 20, 1991

Related U.S. Application Data

[62] Division of Ser. No. 456,491, Dec. 26, 1989, Pat. No. 5,071,991.

[30] Foreign Application Priority Data

Dec. 26, 1988 [FR] France .................. 88 17194

[51] Int. Cl.$^5$ .................. C07D 211/60; C07D 207/12; C07C 255/00; C07C 69/76
[52] U.S. Cl. .................. 546/223; 546/230; 546/243; 546/245; 548/530; 548/543; 548/558; 558/423; 560/23; 560/62
[58] Field of Search .............. 546/223, 230, 243, 245; 548/530, 543, 558; 558/423; 560/23, 62

[56] References Cited

FOREIGN PATENT DOCUMENTS

82689/87 12/1986 Australia .................. 546/269
0273262 7/1988 European Pat. Off. .......... 546/269

OTHER PUBLICATIONS

CA 113:23696x Preparation of . . . agents. Haeusler et al. p. 640, Jun. 1988.
CA 114:61929d Preparation of . . . analogs, Garcia et al. p. 673, Dec. 1988.
Hogberg et al., *acta. Pharm. Suec.*, 13, 427–438 (1976).

*Primary Examiner*—Mary C. Lee
*Assistant Examiner*—Joseph McKane
*Attorney, Agent, or Firm*—Bacon & Thomas

[57] ABSTRACT

The invention describes a method of synthesizing a compound of the formula

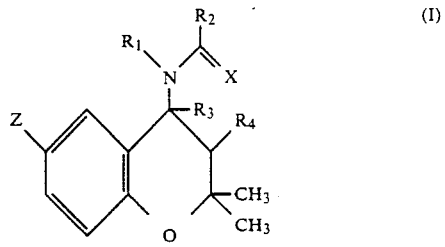

in which
X = O or NR,
Z = an electron-attracting group,
R = H, CN or NO$_2$,
R$_1$ + R$_2$ + N—C≡X = a 5-membered or 6-membered heterocycle, and
R$_3$ = H, R$_4$ = OH or R$_3$ + R$_4$ = a bond, said method involving intermediates of the formula

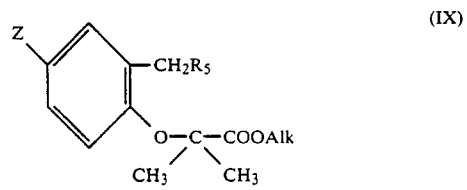

in which R$_5$ = H, Br or N(R$_1$)CXR$_2$.

This method of synthesis does not involve the epoxide derivative of the chroman.

The novel compounds of formula (IX) form a further subject of the invention.

2 Claims, No Drawings

METHOD OF PREPARING CHROMAN DERIVATIVES, AND SYNTHESIS INTERMEDIATES

This application is a division of application Ser. No. 07/456,491, filed Dec. 26, 1989, now U.S. Pat. No. 5,071,991.

The present invention relates to a novel method of synthesizing chroman derivatives. It further relates to novel compounds which are intermediates in this synthesis.

Some chroman derivatives have been described for their antihypertensive activity, especially in J. Med. Chem., 1986, 29, 2194-2201.

These compounds are also described in several European patent applications, for example 76 075, 93 535, 273 262, 296 975 and 312 432.

Several possible methods of synthesis are described in these patent applications. They all involve the epoxide derivative of the chroman. For example, a chromanol derivative can be prepared by reacting a nitrogen heterocycle with the epoxide of the chroman according to the following reaction scheme:

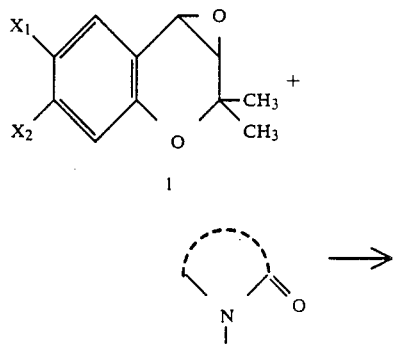

Under the operating conditions described (European patent application 76075), the chroman-3-ol obtained has the trans configuration.

The preparation of the epoxide 1 proceeds via the intermediate preparation of a chromene of the formula

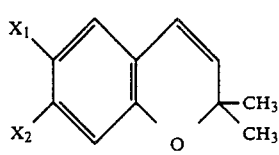

which is in danger of exploding or decomposing when distilled.

According to the present invention, a method of synthesis has now been found which avoids the preparation of the epoxide 1 and the chromene 2.

The present invention relates to a method of preparing a compound of the formula

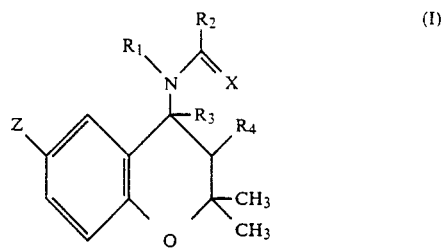

in which:
X is an oxygen atom or a group NR,
Z is an electron-attracting group,
R is hydrogen, a cyano group or a nitro group,
$R_1$ and $R_2$ form a 5-membered or 6-membered heterocycle with the group —N—CX— to which they are bonded, and
$R_3$ is hydrogen and $R_4$ is a hydroxyl group, or $R_3$ and $R_4$ together form a bond.

The compounds (I) in which the group Z is a halogen atom, a nitro group or a cyano group are preferred.

The compounds (I) in which Z is a cyano group are particularly preferred.

The compounds (I) in which the heterocyclic radical formed by the group —N($R_1$)—CO—$R_2$ is 1,2-dihydro-2-oxopyrid-1-yl or 2-oxopyrrolidin-1-yl are particularly preferred.

In the method according to the invention:

a) a 2-methylphenol substituted in the 4-position by the group Z is etherified in a basic medium with ethyl 2-bromo-2-methylpropionate or methyl 2-bromo-2-methylpropionate according to the following reaction scheme:

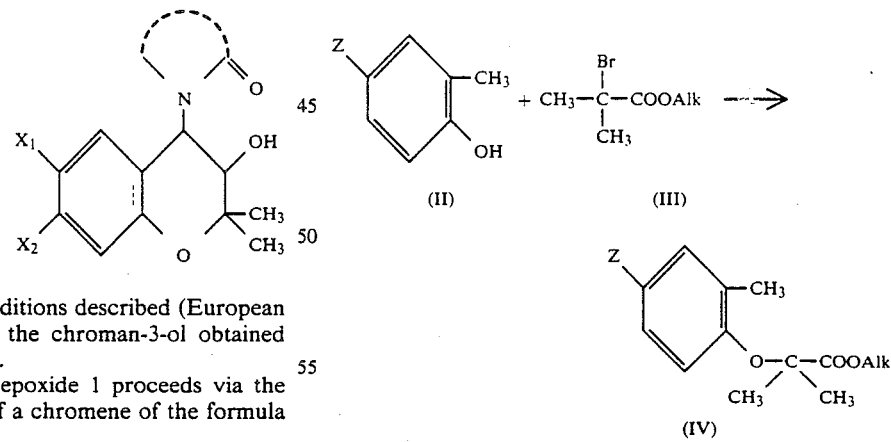

Alk = $CH_3$ or $CH_2CH_3$ b) if appropriate, the compound (IV) in which Z=Br is converted into a compound (IV) in which Z=CN by reaction with cuprous cyanide in an inert solvent, under hot conditions, in the presence of a catalyst which complexes copper;

c) the compound (IV) is brominated with N-bromosuccinimide in a solvent, in the presence of a catalyst and under irradiation with UV rays;

d) an appropriate nitrogen heterocycle of the formula

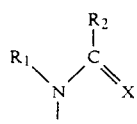
(V)

in which X, $R_1$ and $R_2$ are as defined above for (I), is reacted with the compound obtained in step c), of the formula

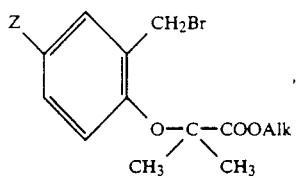
(VI)

the reaction being carried out in the presence of a basic condensation agent, in an inert solvent;

e) the resulting compound of the formula

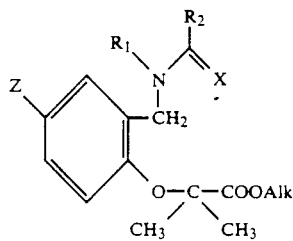
(VII)

is cyclized by heating in a solvent, in a basic medium;

f) the oxo group of the resulting compound of the formula

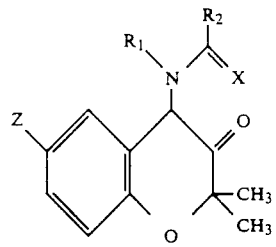
(VIII)

is reduced in the presence of a catalyst such as an alkali metal borohydride, in an alcoholic solvent, to give a compound (I) in which $R_3=H$ and $R_4=OH$, in the form of a cis/trans mixture of the chroman-3-ol;

g) if necessary, the cis and trans isomers of the compound (I) obtained above are separated by known methods; and h) finally, if appropriate, the compound obtained in step f) or g) is dehydrated in an inert solvent, in an alkaline medium, at a temperature of between 50° and 100° C., to give the compound (I) in which $R_3$ and $R_4$ form a bond.

In step a), the reaction is carried out under hot conditions, preferably in the presence of potassium carbonate or potassium hydroxide, if appropriate in a solvent, for example methanol or ethanol, and if appropriate in the presence of a catalyst such as a phase transfer catalyst, for example trimethylbenzylammonium hydroxide.

In step b), the substitution of bromine by cyano, if appropriate, is carried out by choosing tris-3,6-dioxaheptylamine as the preferred catalyst, in a solvent such as dimethylformamide.

According to the invention, the compound (IV) in which $Z=CN$ can therefore be obtained by 2 different synthetic routes:

either direct from the compound (II) in which $Z=CN$, according to step a), or in 2 steps—a)+b)—from the compound (II) in which $Z=Br$.

In step c), the preferred bromination catalyst is benzoyl peroxide used in a solvent such as carbon tetrachloride.

In step d), a metal hydride, for example sodium hydride, can be used as the condensation agent; the reaction is preferably carried out in dimethylformamide.

In step e), the cyclization of the compound (VII) can be carried out in the presence of a metal hydride or, preferably, in the presence of a metal alcoholate such as for example, potassium tert-butylate, in a solvent such as tetrahydrofuran or dioxane.

In step f), the reduction of the oxo group of the compound (VIII) can be carried out in the presence of sodium borohydride in methanol or ethanol.

In step h), the dehydration is preferably carried out under hot conditions, in the presence of an alkali metal hydride such as for example sodium hydride, in a solvent such as tetrahydrofuran or dioxane.

Preferably, the method according to the invention is used to prepare 6-cyano-4-(1,2-dihydro-2-oxopyrid-1-yl)-2,2-dimethyl-3-hydroxychroman, in the cis and trans forms, and 6-cyano-4-(1,2-dihydro-2-oxopyrid-1-yl)-2,2-dimethylchromene. In this case, the nitrogen heterocycle (V) added in step 4 is 2-hydroxypyridine.

The starting materials are known or obtained by known methods.

Thus 4-nitro-2-methylphenol is known and is prepared from the corresponding aniline, which is commercially available.

4-Bromo-2-methylphenol is described in J. Prakt. Chem., 1888, [2]38, 324; it is prepared from 4-bromo-2-methylaniline.

4-Cyano-2-methylphenol is prepared from 4-bromo-2-methylphenol by the method described in J. Org. Chem., 1957, 1669.

An article published in Acta Pharm. Suec., 1976, 13, 427-438, describeds some 2-phenoxy-2-methylpropionic acid derivatives of the formula

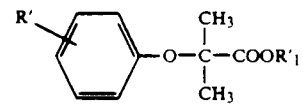

Only two of the compounds described carry a further substituent R' on the benzene ring, and in particular a compound 3, in which $R'=4$-Cl, $R''=2$-$CH_3$ and $R'_1=C_2H_5$. These compounds are potential hypolipidemic agents.

The compounds of the formula

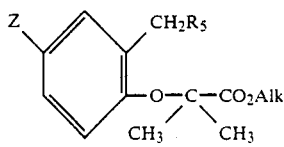

in which Z and Alk are as defined above and $R_5$ is hydrogen, a bromine atom or a group $N(R_1)CXR_2$, X being as defined above, are novel provided that Z is other than a chlorine atom when $R_5$ is hydrogen and Alk is an ethyl group. These novel compounds represent a further feature of the present invention.

The following Example illustrates the invention. The compounds obtained are characterized by their melting point (m.p.), their boiling point (b.p.) or their infra-red spectrum (IR). Furthermore, the NMR spectra were run and they correspond to the structures of the compounds described.

EXAMPLE

6-Cyano-4-(1,2-dihydro-2-oxopyrid-1-yl)-2,2-dimethylchromene

A) Ethyl 2-(4-bromo-2-methylphenoxy)-2-methylpropionate

A mixture containing 105.6 g of 4-bromo-2-methylphenol and 220.4 g of ethyl 2-bromo-2-methylpropionate is heated to 120° C., 78.1 g of potassium carbonate are added slowly and the resulting mixture is then heated at 110° C. for 5 hours. The temperature is lowered to 100° C. and the reaction medium is then diluted with 1.5 liters of aqueous ethanol and then acidified to pH 2, at 80° C., with concentrated sulfuric acid. After concentration of the solvent under vacuum, the residue is taken up with water and ethyl ether. Gel formation is observed. After decantation, the organic phase is washed with a 4% solution of sodium hydroxide and then with water. It is dried over sodium sulfate and the solvent is then concentrated under vacuum.

The orange oil recovered (150 g) is distilled under vacuum to give 120 g of a clear oil.

B.p.: 120°–130° C. under 20 Pa (0.15 mm Hg)
IR: 1730 cm$^{-1}$
Rf (CH$_2$Cl$_2$/hexane: 5/5): 0.46
Yield: 71%

B) Ethyl 2-(4-cyano-2-methylphenoxy)-2-methylpropionate

A mixture containing 29 g of the compound prepared in the previous step and 15 g of cuprous cyanide in 50 ml of tris-3,6-dioxaheptylamine and 100 ml of dimethylformamide is refluxed for 12 hours. It is cooled and then poured into a mixture of one liter of water and 500 ml of ethyl acetate. The resulting mixture is stirred for half an hour and then filtered on diatomaceous silica (Célite ®). After decantation, the organic phase is washed with water (twice), dried over sodium sulfate and concentrated. The oil obtained is filtered on a silica column using isopropyl ether as the eluent to remove the copper salts. Crystallization from hexane gives 18.5 g of the expected product.

M.p.: 46° C.
IR: 2230 cm$^{-1}$
Rf (hexane/acetone: 70/30): 0.38
Yield: 77%

An alternate method of preparing this compound is described below.

A mixture containing 5 g of 4-cyano-2-methylphenol, 2.8 g of potassium hydroxide, 14.5 g of ethyl 2-bromo-2-methylpropionate, 50 ml of ethanol and 0.5 ml of Aliquot 336 ®, a quaternary ammonium compound marketed by ALDRICH, is refluxed for 8 hours. The solvent is concentrated and the residue is then taken up with 100 ml of water. Extraction is carried out with ethyl ether and the organic phase is washed with a 1N solution of sodium hydroxide and then with water. It is dried over sodium sulfate and concentrated. The product obtained is then purified by chromatography on a silica column using pentane as the eluent. 4.3 g of the expected compound are collected.

M.p.: 44° C.
Yield: 60%

C) Ethyl 2-(2-bromomethyl-4-cyanophenoxy)-2-methylpropionate

A mixture containing 15 g of the compound obtained in the previous step and 13.5 g of N-bromosuccinimide in 200 ml of carbon tetrachloride and 20 mg of benzoyl peroxide is refluxed for 3 hours under irradiation with UV rays. It is cooled and then washed with water (twice), dried over sodium sulfate and concentrated. The residue is recrystallized from an isopropyl ether/hexane mixture (50/100) to give 15 g of the expected product.

M.p.: 72° C.
Rf (hexane/acetone: 70/30): 0.31
Yield: 75.8%

D) Ethyl 4-cyano-2-[(1,2-dihydro-2-oxopyrid-1-yl)methyl]-2-phenoxy-2-methylpropionate 900 mg of sodium hydride are added in small portions to a solution of 3 g of 2-hydroxypyridine in 50 ml of dimethylformamide and the mixture is then stirred for 30 minutes at room temperature. 9 g of the compound obtained in the previous step are added and the mixture is then stirred for 16 hours at room temperature and 2 hours at 60° C. The dimethylformamide is concentrated and the residue is then taken up in water and extracted with ethyl ether (twice). The organic phase is washed with water and then dried over sodium sulfate. The oil obtained (9 g) is purified by chromatography on a silica column using ethyl acetate as the eluent. 6.5 g of the expected product are collected.

M.p.: 73.1° C.
Rf (ethyl acetate): 0.28
Yield: 69.1%

E) 6-Cyano-4-(1,2-dihydro-2-oxopyrid-1-yl)-2,2-dimethyl-3-oxochroman 750 mg of potassium tert-butylate are added in small portions to a solution of 2 g of the compound obtained in the previous step in 50 ml of tetrahydrofuran. The mixture is stirred for 4 hours at room temperature. The solvent is concentrated and the residue is taken up with 50 ml of water and then acidified with concentrated hydrochloric acid. Extraction is carried out with ethyl ether and the organic phase is washed with water, dried over sodium sulfate and concentrated. The oil obtained is purified by chromatography on a silica column using a CH$_2$Cl$_2$/CH$_3$OH mixture (99/1) as the eluent. Recrystallization from isopropyl ether gives 950 mg of the expected product.

M.p.: 178° C.

Yield: 56%

F) Cis- and trans-6-cyano-4-(1,2-dihydro-2-oxopyrid-1-yl)-2,2-dimethyl-3-hydroxychroman 1.7 g of the compound obtained in the previous step are mixed with 45 ml of methanol, 0.114 g of sodium borohydride is added at room temperature and the mixture is then stirred for 3 hours at room temperature. The excess reagent is destroyed by the addition of acetic acid and the solvent is then concentrated under vacuum. The residue is taken up with water and then extracted with ethyl acetate. The organic phase is washed with water, dried over sodium sulfate and then concentrated under vacuum. The expected product is recovered in the form of a white solid foam, which is used as such in the next step.

Rf ($CH_2Cl_2/CH_3OH$: 95/5): 0.34

Yield: 82%

G) 6-Cyano-4-(1,2-dihydro-2-oxopyrid-1-yl)-2,2-dimethylchromene 1.4 g of the compound obtained in the previous step are added to 44 ml of anhydrous tetrahydrofuran, 0.132 g of sodium hydride as a 50% suspension in oil is added in portions at room temperature and the mixture is then refluxed for 5 hours. The solvent is concentrated under vacuum, the residue is taken up with methylene chloride and the organic phase is then washed with water until the washings are neutral, and dried over sodium sulfate.

After concentration under vacuum, 1 g of the expected product is recovered in the form of a white solid.

M.p.: 151° C.

Yield: 73%

What is claimed is:

1. A synthesis intermediate compound for the preparation of a compound having the formula:

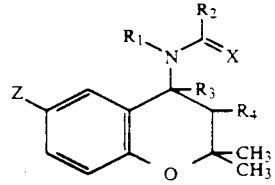

said synthesis intermediate compound having the formula (IX):

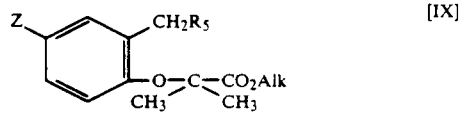

in which

X is oxygen or a group N=R,

Z is an electron attracting group,

R is a hydrogen atom, a nitro or a cyano group,

Alk is a methyl or an ethyl, and $R_1$ and $R_2$ form a 5-membered or 6-membered heterocycle with the group —N—CX— to which they are bonded.

$R_3$ is hydrogen and $R_4$ is an hydroxyl group or $R_3$ and $R_4$ together form a bond, $R_5$ is hydrogen, a bromine atom or a group $N(R_1)CXR_2$, provided that Z is other than a chlorine atom when $R_5$ is hydrogen and Alk is an ethyl group.

2. A compound of formula (IX) according to claim 1 in which Z is a cyano group and $R_5$ is hydrogen, a bromine atom or a 1,2-dihydro-2-oxopyrid-1-yl group.

* * * * *